(12) United States Patent
Grifantini et al.

(10) Patent No.: US 6,566,105 B1
(45) Date of Patent: May 20, 2003

(54) PROCESS FOR THE PRODUCTION OF D-α-AMINO ACIDS

(75) Inventors: Renata Grifantini, Milan (IT); Gianni Frascotti, Milan (IT); Giuliano Galli, San Donato Milanese (IT); Guido Grandi, Segrate (IT)

(73) Assignee: Eniricerche S.p.A., San Donato Milanese (IT)

( * ) Notice: Subject to any disclaimer, the term of this patent is extended or adjusted under 35 U.S.C. 154(b) by 0 days.

(21) Appl. No.: 08/415,658

(22) Filed: Apr. 3, 1995

(30) Foreign Application Priority Data

Apr. 15, 1994 (IT) .......................................... MI94A0726

(51) Int. Cl.$^7$ ......................... C12P 13/04; C12N 15/00; C12N 9/86
(52) U.S. Cl. ................ 435/106; 435/320.1; 435/252.31; 435/252.33; 435/231; 536/23.2
(58) Field of Search ................................. 435/106, 280, 435/320.1, 252.31, 252.33, 231; 536/23.2

(56) References Cited

U.S. PATENT DOCUMENTS 4,312,948 A * 1/1982 Olivieri et al. ............. 435/253

FOREIGN PATENT DOCUMENTS

| EP | 0515698 | * | 12/1992 |
| WO | 9400577 | * | 1/1994 |

* cited by examiner

*Primary Examiner*—Rebecca E. Prouty
*Assistant Examiner*—David Steadman
(74) *Attorney, Agent, or Firm*—Oblon, Spivak, McClelland, Maier & Neustadt, P.C.

(57) ABSTRACT

A process is described for the production of D-α-amino acids by the stereospecific conversion of racemic mixtures of 5-substituted hydantoins using a microorganism transformed with a plasmid which expresses an enzymatic system which converts the hydantoins into the corresponding D-α-amino acids without the requirement for inducers. Also described is a plasmid containing genes encoding the enzymatic system, and a microorganism transformed with the plasmid.

15 Claims, 8 Drawing Sheets

```
ATG ACA CGT CAG ATG ATA CTT GCT GTC GGA CAG CAA GGC CCC ATC   45
Met Thr Arg Gln Met Ile Leu Ala Val Gly Gln Gln Gly Pro Ile
                 5                  10                  15
GCG CGA GCG GAG ACA CGC GAA CAG GTG GTT GGC CGC CTC CTC GAC   90
Ala Arg Ala Glu Thr Arg Glu Gln Val Val Gly Arg Leu Leu Asp
                20                  25                  30
ATG TTG ACG AAC GCA GCC AGC CGG GGC GTG AAC TTC ATC GTC TTT  135
Met Leu Thr Asn Ala Ala Ser Arg Gly Val Asn Phe Ile Val Phe
                35                  40                  45
CCC GAG CTT GCG CTC ACG ACC TTC TCC CCG CGC TGG CAT TTC ACC  180
Pro Glu Leu Ala Leu Thr Thr Phe Phe Pro Arg Trp His Phe THr
                50                  55                  60
GAC GAG GCC GAG CTC GAT AGC TTC TAT GAG ACC GAA ATG CCC GGC  225
Asp Glu Ala Glu Leu Asp Ser Phe Tyr Glu Thr Glu Met Pro Gly
                65                  70                  75
CCG GTG GTC CGT CCA CTC TTT GAG ACG GCC GCC GAA CTC GGG ATC  270
Pro Val Val Arg Pro Leu Phe Glu Thr Ala ala Glu Leu Gly Ile
                80                  85                  90
GGC TTC AAT CTG GGC TAC GCC GAA CTC GTC GTC GAA GGC GGC GTC  315
Gly Phe Asn Leu Gly Tyr Ala Glu Leu Val Val Glu Gly Gly Val
                95                 100                 105
AAG CGT CGC TTC AAC ACG TCC ATT CTG GTG GAT AAG TCA GGC AAG  360
Lys Arg Arg Phe Asn Thr Ser Ile Leu Val Asp Lys Ser Gly Lys
               110                 115                 120
ATC GTC GGC AAG TAT CGT AAG ATC CAT TTG CCG GGT CAC AAG GAG  415
Ile VAl Gly Lys Tyr Arg Lys Ile His Leu Pro Gly Hys Lys Glu
               125                 130                 135
TAC GAG GCC TAC CGG CCG TTC CAG CAT CTT GAA AAG CGT TAT TTC  450
Tyr Glu Ala Tyr Arg Pro Phe Gln His Leu Glu Lys Arg Tyr Phe
               140                 145                 150
```

*FIG. 4A*

```
GAG CCG GGC GAT CTC GGC TTC CCG GTC TAT GAC GTC GAC GCC GCG   495
Glu Pro Gly Asp Leu Gly Phe Pro Val Tyr Asp Val Asp Ala Ala
                155                 160                 165
AAA ATG GGG ATG TTC ATC TGC AAC GAT CGC CGC TGG CCT GAA ACG   540
Lys Met Gly Met Phe Ile Cys Asn Asp Arg Arg Trp Pro Glu Thr
                170                 175                 180
TGG CGG GTG ATG GGA CTT AAG GGC GCC GAG ATC ATC TGC GGC GGC   585
Trp Arg Val Met Gly Leu Lys Gly Ala Glu Ile Ile Cys Gly Gly
                185                 190                 195
TAC AAC ACG CCG ACC CAC AAT CCC CCC GTT CCC CAG CAC GAC CAT   630
Tyr Asn Thr Pro Thr His Asn Pro Pro Val Pro Gln His Asp His
                200                 205                 210
CTG ACG TCC TTC CAC CAC CTT CTG TCG ATG CAG GCC GGG TCG TAC   675
Leu Thr Ser Phe His His Leu Leu Ser Met Gln Ala Gly Ser Tyr
                215                 220                 225
CAA AAC GGC GCC TGG TCC GCG GCG GCC GGC AAG GTC GGC ATG GAG   720
Gln Asn Gly Ala Trp Ser Ala Ala Ala Gly Lys Val Gly Met Glu
                230                 235                 240
GAG GGG TGC ATG CTG CTC GGC CAT TCG TGC ATC GTG GCG CCG ACC   765
Glu Gly Cys Met Leu Leu Gly His Ser Cys Ile Val Ala Pro Thr
                245                 250                 255
GGC GAA ATC GTT GCC CTG ACC ACG ACG TTG GAA GAC GAG GTG ATC   810
Gly Glu Ile Val Ala Leu Thr Thr Thr Leu Glu Asp Glu Val Ile
                260                 265                 270
ACC GCC GCC GTC GAT CTC GAC CGC TGC CGG GAA CTG CGC GAA CAC   855
Thr Ala Ala Val Asp Leu Asp Arg Cys Arg Glu Leu Arg Glu His
                275                 280                 285
ATC TTC AAT TTC AAA GCC CAT CGT CAG CCA CAG CAC TAC GGT CTG   900
Ile Phe Asn Phe Lys Ala His Arg Gln Pro Gln His Tyr Gly Leu
                290                 295                 300
ATC GCG GAA TTT TGA                                           915
Ile Ala Glu Phe STOP
```

*FIG. 4B*

```
ATG GAT ATC ATC ATC AAG AAC GGA ACC ATC GTA ACC GCG GAC GGG   45
Met Asp Ile Ile Ile Lys Asn Gly Thr Ile Val Thr Ala Asp Gly
                5                   10                  15
ATT TCT CCC GCC GAT CTC GGA ATC AAG GAT GGC AAG ATC GCC CAG   90
Ile Ser Pro Ala Asp Leu Gly Ile Lys Asp Gly Lys Ile Ala Gln
                20                  25                  30
ATC GGC GGA ACG TTC GGC CCG GCC GGC CGG ACA ATC GAC GCC TCC  135
Ile Gly Gly Thr Phe Gly Pro Ala Gly Arg Thr Ile Asp Ala Ser
                35                  40                  45
GGC CGC TAC GTT TTT CCG GGC GGC ATC GAC GTT CAT ACG CAT GTC  180
Gly Arg Tyr Val Phe Pro Gly Gly Ile Asp Val His Thr His Val
                50                  55                  60
GAG ACG GTC AGC TTC AAC ACG CAG TCG GCC GAC ACA TTC GCA ACC  225
Glu Thr Val Ser Phe Asn Thr Gln Ser Ala Asp Thr Phe Ala Thr
                65                  70                  75
GCG ACG GTC GCG GCC GCC TGT GGC GGC ACG ACG ACC ATC GTC GAT  270
Ala Thr Val Ala Ala Ala Cys Gly Gly Thr Thr Thr Ile Val Asp
                80                  85                  90
TTC TGC CAG CAG GAC CGC GGC CAT AGC CTG AGG GAG GCG GTC GCC  315
Phe Cys Gln Gln Asp Arg Gly Hys Ser Leu Arg Glu Ala Val Ala
                95                  100                 105
AAA TGG GAC GGC ATG GCC GGC GGC AAG TCG GCG ATC GAC TAC GGC  360
Lys Trp Asp Gly Met Ala Gly Gly Lys Ser Ala Ile Asp Tyr Gly
                110                 115                 120
TAC CAT ATC ATC GTG CTC GAT CCG ACT GAT AGC GTG ATC GAG GAG  405
Tyr His Ile Ile Val Leu Asp Pro Thr Asp Ser Val Ile Glu Glu
                125                 130                 135
CTA GAG GTA CTG CCA GAT CTC GGC ATC ACC TCC TTC AAG GTC TTC  450
Leu Glu Val Leu Pro Asp Leu Gly Ile Thr Ser Phe Lys Val Phe
```

*FIG. 5A*

```
                140                        145                        150
ATG GCT TAT CGC GGC ATG AAC ATG ATC GAC GAC GTG ACA CTG CTC  495
Met Ala Tyr Arg Gly Met Asn Met Ile Asp Asp Val Thr Leu Leu
                155                        160                        165
AGG ACG CTC GAC AAG GCC GCC AAG ACT GGG TCA CTC GTC ATG GTG  540
Arg Thr Leu Asp Lys Ala Ala Lys Thr Gly Ser Leu Val Met Val
                170                        175                        180
CAC GCG GAG AAC GGG GAC GCC GCC GAC TAT CTT CGC GAC AAG TTC  585
His Ala Glu Asn Gly ASp Ala Ala Asp Tyr Leu Arg Asp Lys Phe
                185                        190                        195
GTC GCC GAT GGC AAA ACG GCG CCG ATC TAC CAC GCG CTC AGC CGT  630
Val Ala Asp Gly Lys Thr Ala Pro Ile Tyr HIs Ala Leu Ser Arg
                200                        205                        210
CCG CCC CGG GTC GAA GCC GAG GCG ACC GCG AGG GCC CTC GCC CTG  675
Pro Pro Arg Val Glu Ala Glu Ala Thr Ala Arg Ala Leu Ala Leu
                215                        220                        225
GCG GAA ATC GTC AAC GCC CCG ATC TAC ATC GTG CAT CTG ACC TGC  720
Ala Glu Ile Val Asn Ala Pro Ile Tyr Ile Val His Leu Thr Cys
                230                        235                        240
GAA GAA TCC TTC GAC GAG TTG ATG CGG GCA AAG GCT CGG GGT GTC  765
Glu Glu Ser Phe Asp Glu Leu Met Arg Ala Lys Ala Arg Gly Val
                245                        250                        255
CAC GCC CTG GCC GAA ACC TGC ACA CAA TAC CTC TAC CTC ACC AAG  810
His Ala Leu Ala Glu Thr Cys Thr Gln Tyr Leu Tyr Leu Thr Lys
                260                        265                        270
GAC GAC CTG GAG CGG CCG GAT TTC GAG GGC GCG AAG TAT GTT TTC  855
Asp Asp Leu Glu Arg Pro Asp Phe Glu Gly Ala Lys Tyr VAl Phe
                275                        280                        285
ACC CCG CCT CCG CGC ACG AAG AAG GAC CAG GAA ATC CTC TGG AAC  900
Thr Pro Pro Pro Arg Thr Lys Lys Asp Gln Glu Ile Leu Trp Asn
                290                        295                        300
GCA CTC CGG AAC GGG GTC CTC GAA ACG GTC TCC TCG GAC CAT TGT  945
Ala Leu Arg Asn Gly Val Leu Glu Thr Val Ser Ser Asp His Cys
```

*FIG. 5B*

```
                              305                          310                               315
TCC TGG CTC TTC GAG GGG CAC AAG GAT CGG GGC AGG AAC GAC TTC  990
Ser Trp Leu Phe Glu Gly His Lys Asp Arg Gly Arg Asn Asp Phe
                              320                          325                               330
CGC GCC ATC CCG AAC GGA GCG CCG GGC GTC GAG GAG CGG CTG ATG 1035
Arg Ala Ile Pro Asn Gly Ala Pro Gly VAl Glu Glu Arg Leu Met
                              335                          340                               345
ATG GTC TAT CAG GGC GTC AAC GAA GGC CGC ATT TCC CTC ACC CAG 1080
Met Val Tyr Gln Gly Val Asn Glu Gly Arg Ile Ser Leu Thr Gln
                              350                          355                               360
TTC GTA GAA CTG GTC GCC ACG CGC CCG GCC AAG GTC TTC GGC ATG 1125
Phe Val glu Leu Val Ala Thr Arg Pro Ala Lys Val Phe Gly Met
                              365                          370                               375
TTC CCG GAA AAA GGA ACG GTC GCG GTC GGT TCG GAT GCC GAC ATC 1170
Phe Pro Glu Lys Gly Thr Val Ala Val Gly Ser Asp Ala Asp Ile
                              380                          385                               390
GTC CTT TGG GAT CCC GAG GCT GAA ATG GTG ATC GAA CAA AGC GCC 1215
Val Leu Trp Asp Pro Glu Ala Glu Met Val Ile Glu Gln Ser Ala
                              395                          400                               405
ATG CAT AAC GCC ATG GAT TAC TCC TCC TAC GAG GGA CAC AAG ATC 1260
Met His Asn Ala Met Asp Tyr Ser Ser Tyr Glu Gly His Lys Ile
                              410                          415                               420
AAG GGC GTG CCG AAG ACA GTG CTG CTG CGT GGC AAG GTG ATC GTC 1305
Lys Gly Val Pro Lys Thr Val Leu Leu Arg Gly Lys Val Ile Val
                              425                          430                               435
GAC GAG GGA ACC TAC GTG GGG GCG CCG ACG GAT GGC CAG TTC CGG 1350
Asp Glu Gly Thr Tyr Val Gly Ala Pro Thr Asp Gly Gln Phe Arg
                              440                          445                               450
AAG CGG CGG AAA TAC AAG CAA TAA                             1373
Lys Arg Arg Lys Tyr Lys Gln STOP
                              455
```

*FIG. 5C*

PROCESS FOR THE PRODUCTION OF D-α-AMINO ACIDS

The present invention relates to a process for the production of D-α-amino acids by the stereospecific conversion of racemic mixtures of 5-substituted hydantoins with a microorganism transformed with a plasmid capable of espressing in high yields and without inducers an enzymatic system capable of directly converting said hydantoins into the corresponding D-α-amino acids.

The term enzymatic system refers to a system consisting of D-hydantoinase and D-N-carbamylase enzymes.

D-α-amino acids are extremely valuable compounds useful for the preparation of pharmacologically active substances (for example, D-phenylglycine and D-para-hydroxyphenylglycine are used in the synthesis of penicillins and cephalosporins), pesticides (D-valine for the synthesis of the insecticide fluvanilate) or sweeteners (D-alanine).

The preparation of D-α-amino acids by the chemical and/or enzymatic hydrolysis of the corresponding 5-substituted hydantoins is known in the art.

For example patent FR 2.310.986 describes a process wherein 5-substituted hydantoins are chemically hydrolized into racemic mixtures of D,L amino acids which are subsequently subjected to a separation treatment of the isomer of interest.

Patent FR 2.317.357, on the contrary, describes a process wherein racemic mixtures of 5-substituted hydantoins are subjected to enzymatic hydrolysis and, subsequently, the products of this transformation (N-carbamyl-D-α-amino acids) are chemically oxidized into the corresponding D-α-amino acids.

The problems relating to these processes generally consist in the fact that they require complex procedures for the resolution and purification of the D-α-amino acids. As a result these processes are not of economical interest from an industrial point of view.

Processes are described in the art wherein D-α-amino acids are obtained directly from 5-substituted hydantoins by the treatment of these with enzymatic systems prepared from microorganisms such as Paeudomonas, Moraxella, Agrobacterium, Hansenula, Arthrobacter (EP-199.943, EP-309.310, U.S. Pat. No. 4,312,948, FR 2456728).

The preparation of these enzymatic systems, however, requires the use of efficient inducers capable of stimulating the production of these enzymes on the part of the microorganisms. It is, in fact, known that the expression level of the enzymes D-hydantoinase and D-N-carbamylase is constitutively very low (Syldatk et al. (1990), "Advances in Biochem. Engineering/Biotechnology (Fiechter, A. Ed.), 41, pages 29–75, Springer-Verlag, Berlin).

The inducers normally used are derivatives of hydantoins or nitrogenated cyclic compounds which are howeveny easily metabolized by the microorganisms, or compounds such as uracil or thio-2-uracil or thymine which are not metabolized (Meyer et al., (1993), Fems Microbiol. Letters, 109: 67–74).

The use of inducers creates a series of drawbacks among which an increase in the production costs and a certain variability in the production yields of the enzymes. In addition, the expression level which can be obtained in most of the microorganisms following induction is insufficient for economical use in industrial processes (Syldatk et al. (1987), Biotechnol. lett., 9: 25–30; Yokozeki et al. (1987) Agric. Biol. Chem., 51, 715–722).

Recently the genes which encode the enzymes D-hydantoinase and D-N-carbamylase have been individually sequenced and cloned (U.S. Pat. No. 4,912,044 and EP-515-698).

More specifically, patent U.S. Pat. No. 4,912,044 describes the preparation of D-hydantoinase by the fermentation of a microorganism transformed with a hybrid vector containing the hydantoinase gene whose expression is induced by temperature variation. The enzyme thus obtained is used for the production of D-N-carbamyl derivatives from 5-substituted hydantoins.

Patent application EP-515.698 describes, on the other hand, the preparation of D-N-carbamylase by the fermentation of a microorganism transformed with a plasmid comprising the carbamylase gene whose expression is chemically induced with IPTG. The enzyme thus obtained is used for the production of D-α-amino acids from N-carbamyl derivatives.

As industrial interest is directed towards the conversion of racemic hydantoins to D-α-amino acids, the fact that the two enzymes are expressed in different strains involves the use of both and consequently the development of a process starting from two distinct fermentative processes.

This obviously increases the production costs and reduces the conversion kinetics. In fact, in order to complete the enzymatic reaction, the N-carbamyl derivative produced by the transformed microorganism containing the hydantoinase must pass through the bacterial membrane, spread into the reaction medium and then proceed in the opposite direction to reach the second enzyme (carbamylase) present in the other strain. All this is particularly penalizing from the point of view of kinetics considering the reduced permeability of the bacterial membranes to the carbamyl derivatives (Olivieri et al. (1981), Biotechnol. Bioeng., 23, 2173–2183) and the inevitable dilution of the carbamyl itself in the reaction mixture.

Finally, the use of a double volume of biomass has a negative influence on the yields and degree of purity of the final product.

In addition, the necessity of having to induce the expression of these enzymes creates a further problem thus making these processes of little interest for practical use.

The object of the present invention is to overcome the disadvantages of the known art described above.

In particular it has now been found, in accordance with the present invention, that the use of a particular plasmid which contains the genes of D-hydantoinase and N-carbamylase put under the control of an appropriate synthetic promoter, enables the high expression of these enzymes to be obtained without inducers.

It is therefore possible to prepare a single microorganism transformed with said plasmid containing the two enzymatic activities inside. This solution solves not only the problems relating to kinetics due to the limited permeability, as the two reactions occur inside the same cell where the concentration of the substrates is excellent, but also those relating to the requirement of inducers and treatment of the product and of the waste products.

In accordance with this, a first aspect of the present invention relates to a process for the production of D-α-amino acids by the stereospecific conversion of racemic mixtures of 5-substituted hydantoins characterized in that, the conversion reaction is carried out in the presence of a microorganism transformed with a plasmid capable of expressing at high levels and without inducers an enzymatic system capable of converting said hydantoins into the corresponding D-α-amino acids.

A further object of the present invention is the plasmid pSM651 comprising the genes which encode the enzymatic system.

Yet another object of the present invention is a microorganism transfored with the plasmid pSM651 capable of expressing with high efficiency and without inducers an enzymatic system capable of stereospecifically converting racemic mixtures of 5-substituted hydantoins into the corresponding D-α-amino acids.

A further object of the present invention relates to the use of said microorganisms or enzymatic system isolated from said microorganisms for the production of D-α-amino acids by the stereospecific conversion of racemic mixtures of 5-substituted hydantoins.

Further objects of the present invention will be evident from the description and examples below.

BRIEF DESCRIPTION OF THE FIGURES

FIGS. 4A–B: Nucleotide and amino acid sequence of carbamylase (SEQ ID NO:18–19).

FIGS. 5A–C: Nucleotide and amino acid sequence of hydantoinase (SEQ ID NO:20–21).

Figure 1:
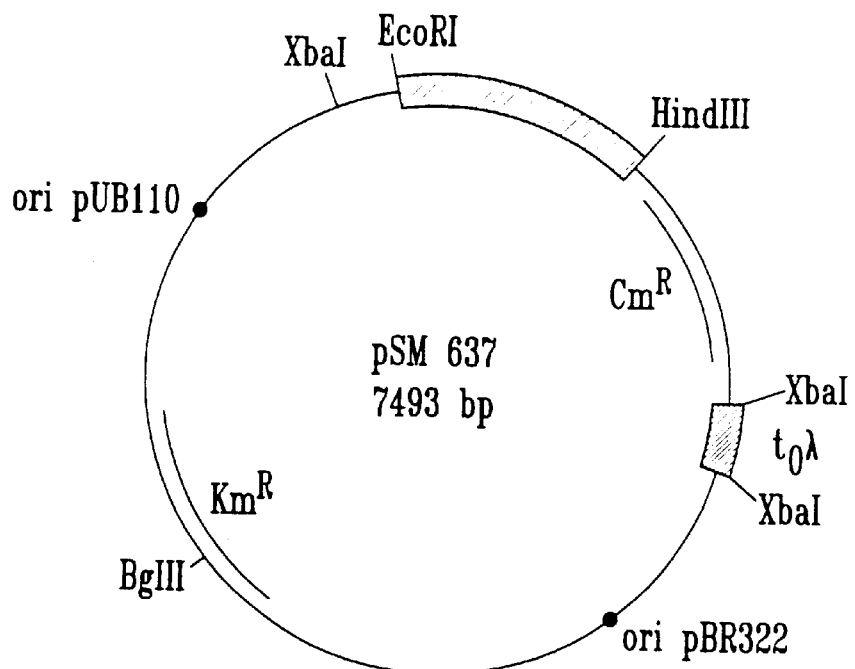
FIG. 1: Map of the plasmid pSM637 containing the carbamylase gene
Figure 2:
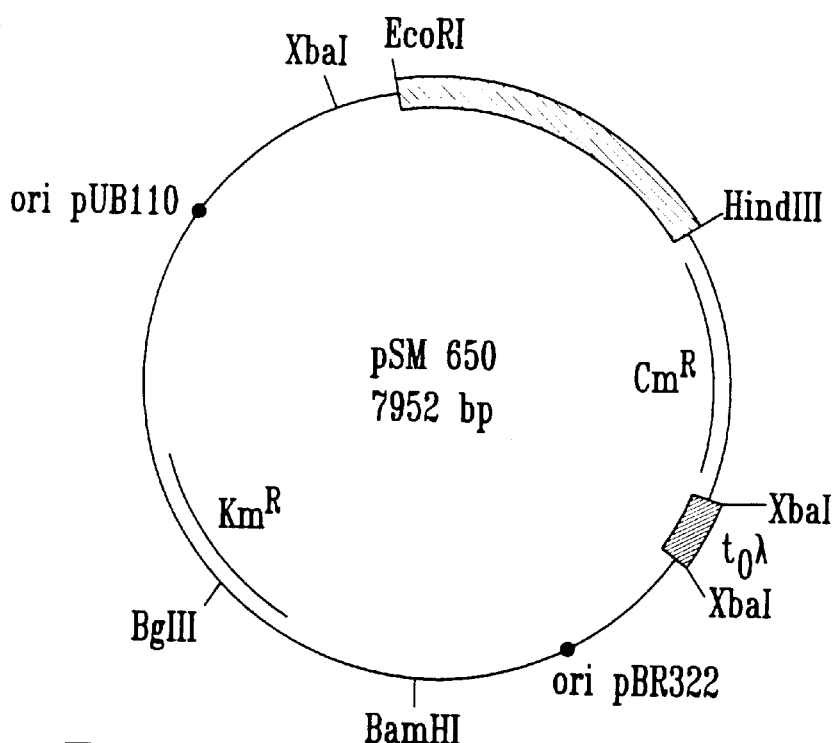
FIG. 2: Map of the plasmid pSM650 containing the hydantoinase gene
Figure 3:
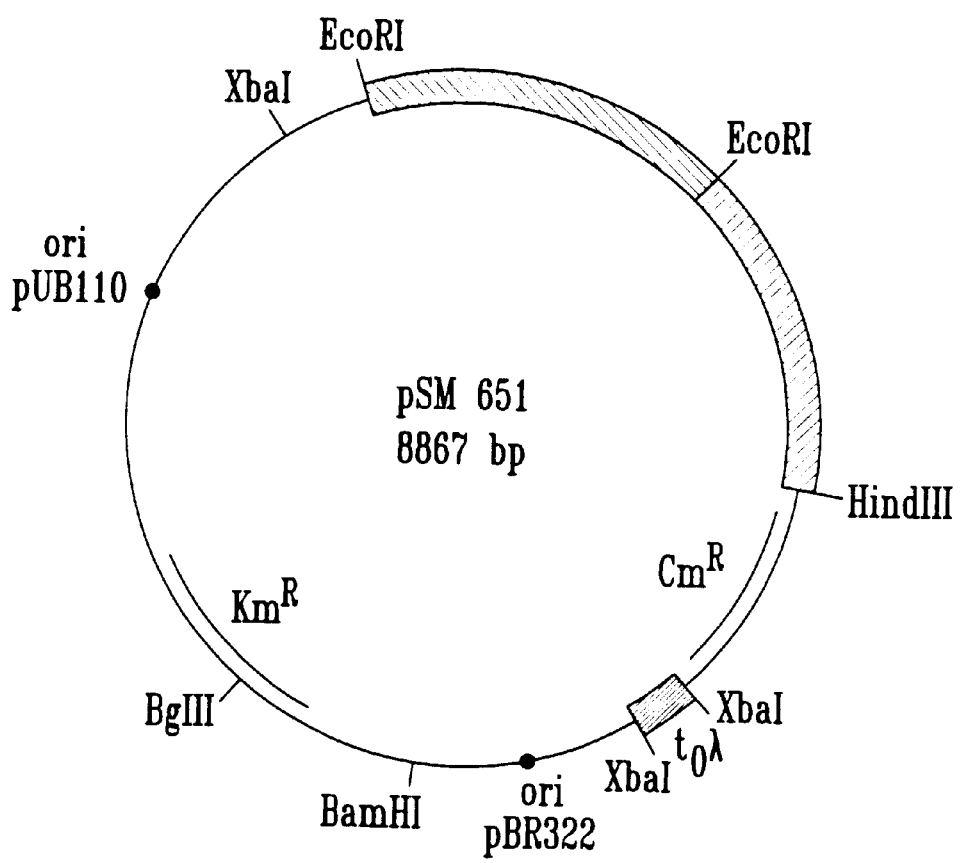
FIG. 3: Map of the plasmid pSM651 containing the hydantoinase-carbamylase operon.

The genes which encode the D-hydantoinase and D-N-carbamylase enzymes can be isolated from microorganisms such as Pseudomonas, Hansenula, Agrobacterium, Aerobacter, Aeromonas, Bacillus, Moraxella, Brevibacterium, Flavobacterium, Serratia, Micrococcus, Arthrobacter or Paracoccus. Specific examples of these microorganisms are *Bacillus macroides* ATCC 12905, *Aerobacter cloacae* IAM 1221, Agrobacterium sp. IP I-671, *Agrobacterium radiobacter* NRRLB 11291, Pseudomonas sp. FERM BP 1900.

The isolation of the genes which encode the D-hydantoinase and D-N-carbamylase enzymes can be carried out by the construction of a gene library, representing the genome of the microorganism, identification of the clones containing the genes which encode said enzymes, analysis of the gene sequence, insertion of said genes into a vector and control of their expression.

The term gene library or genome bank means the combination of clones of a given host microorganism each of which carries a fragment of the chromosomal DNA deriving from the donor organism of which the bank is to be obtained. A bank is defined as being representative when the combination of the single fragments contained in each clone forms the majority of the chromosomal DNA of the donor organism.

According to a preferred embodiment of the process of the present invention, the strain *A.radiobacter* NRRL B-11291 is used as donor organism for the isolation of the genes which encode D-hydantoinase and D-N-carbamylase.

In practice, two genome banks of said microorganism are constructed in *E.coli* by digesting the chromosomal DNA separately with the restriction enzymes BamHI and SacI. Among the fragments obtained with the two digestions, those having dimensions normally of between 3,000 and 4,500 bp are purified. The selection is carried out by estimating the molecular weight of the D-hydantoinase and D-N-carbamylase enzymes of 50,000 and 34,000 Daltons respectively.

The two populations of BamHI and SacI fragments are then ligated to a vector of *E.coli* under such conditions as to facilitate the condensation of a single fragment to each molecule of the vector. The two ligase mixtures are used to transform cells of *E.coli* made competent as shown for example by Dagert, M. and Ehrlich (1979), (Gene, 6:23).

The two populations of colonies (genome banks) thus obtained, each of which carrying a hybrid plasmid i.e. consisting of the molecule of the vector and a chromosomal DNA fragment of *A.radiobacter*, are then selected to identify those clones containing the hydantoinase and carbamylase genes.

The identification can be carried out by direct expression or using specific probes. The second method is preferably used. For the selection of the probes, in the case of carbamylase, reference was made to the knowledge of the amino-end sequence of carbamylase by Comomonas sp. 5222c (Ogawa et al. (1993), Eur. J. Biochem., 212: 685–691).

On the basis of this sequence small oligonucleotides are synthesized which, once marked, are used for the screening of the genothecas by hybridization techniques (Maniatis et al., (1982), "Molecular Cloning: a laboratory manual", Cold Spring Harbor Laboratory).

This permitted the identification of a clone carrying a hybrid plasmid carrying a BamHI fragment containing the nucleotidic sequence which encodes for the whole carbamylase. Analysis of said plasmid showed, in addition, the presence of a second incomplete ORF, placed on the other strand with respect to the carbamylase gene, which showed a homology with urease portions isolated from various microorganisms.

As ureases, like hydantoiases, are enzymes belonging to the group of amido-hydrolases, it was assumed that the incomplete ORF corresponded to that of hydantoise. This assumption was then confirmed by the enzymatic activity tests carried out on cellular extracts of cells carrying the identified gene.

In order to isolate the whole nucleotide sequence encoding hydantoinase, a screening of the gene library of the DNA of *A.radiobacter* digested with SacI was carried out by hybridization with an oligonucleotide synthesized on the basis of the nucleotide sequence of the incomplete ORF.

The screening led to the isolation of a clone containing the whole hydantoinase gene. The genes thus isolated were sequenced using the sequenase version Kit 2.0 sold by United State Biochemical.

For the construction of a plasmid comprising both of the isolated genes vectors selected from plasmids, cosmids and bacteriophages known in the art, can be used.

The bifunctional plasmid of *E.coli* and *B.subtilis*, pSM671 CBS 205.94 is preferably used.

This plasmid, which comprises the genes which encode for resistance to kanamycin and chloramphenicol and has replication origins operable in *E.coli* and *B.subtilis*, is characterized in that it contains a synthetic promoter capable to direct with high efficiency and without inducers, the expression of the genes put under its control.

In practice, the DNA fragments containing the genes which encode the D-hydantoinase and D-N-carbamylase enzymes are cloned into the plasmid pSM671 in the unique restriction sites EcoRI and HindIII obtaining the recombinant plasmid pSM651.

The construction can be carried out operating according to the general techniques known in the field of recombinant DNA. In order to verify whether these enzymes are expressed from B.subtilis and E.coli, cells transformed with said plasmid are cultured in a suitable culture medium. The total proteins, extracted from the cellular lysate, analyzed on polyacrylamide gel showed the presence of two proteins having a molecular weight corresponding to that of the two enzymes; these proteins represent about 10% of the total proteins. These results confirm the capacity of B.subtilis and E.coli to express said enzymes with high efficiency and without inducers.

The enzymatic system of the present invention can be obtained by culturing the strains E.coli or B.subtilis transformed with the plasmid pSM651, under aerobic conditions, in an aqueous medium containing assimilable sources of carbon and nitrogen as well as various cations, anions and, possibly, traces of vitamins, such as biotin, thiamine, or amino acids.

Assimilable carbon sources comprise carbohydrates such as glucose, hydrolized amides, molasses, sucrose or other conventional carbon sources.

Examples of nitrogen sources can be selected, for example, from mineral ammonium salts, such as ammonium nitrate, ammonium sulphate, ammonium chloride or ammonium carbonate and urea or materials containing organic or inorganic nitrogen such as peptone, yeast extract or meat extract.

The following cations and anions are equally suitable for the object of the present invention: potassium, sodium, magnesium, iron, calcium, acid phosphates, sulphates, chlorides, manganese, and nitrates.

The fermentation is carried out, under stirring, at a temperature of between 25° and 40° C., preferably between 30° and 37° C. and at a pH of between 6 and 7.5, preferably between 6.5 and 7.0.

The cells (biomass) recovered from the culture medium by means of the conventional techniques such as centrifugation or filtration are used in the conversion phase of the racemic mixtures of 5-substituted hydantoins.

Alternatively, the conversion reaction can be carried out using either the cellular extract obtained from the disintegration of the cells by sonication or French-Press, or enzymes purified or partially purified with the conventional methods, or enzymes immobilized on insoluble supports.

Numerous hydantoins substituted in position 5 can be used in the process of the present invention. Possible substituents in position 5 are selected from a linear or branched alkyl group with a number of carbon atoms of between 1 and 6, which can be mono or polysubstituted with hydroxy, carboxy, hydrosulphide or amino groups or a phenyl or benzyl group which, in turn, can contain one or more substituents in ortho, meta and para position. Examples of 5-substituted hydantoins are: D,L-5-phenylhydantoin, D,L-5-para-hydroxyphenylhydantoin, D,L-5-methylhydantoin, D,L-5-isopropylhydantoin, D,L-5-thienylhydantoin, D,L-5-para-methoxyphenylhydantoin, D,L-5-para-chloro phenylhydantoin, D,L-5-benzylhydantoin.

The conversion of the hydantoins into the corresponding D-α-amino acids is carried out in a nitrogen atmosphere in a hermetically closed apparatus, at a temperature of between 20 and 60° C., preferably between 30 and 45° C.

The pH of the reaction medium is maintained within values of between 6 and 10 and preferably between 7 and 8.5. This regulation of the pH can be carried out, for example, by adding a base aqueous solution such as an aqueous solution of ammonia, potassium hydroxide, sodium hydroxide, sodium or potassium carbonate.

The initial concentration of the hydantoins is generally between 2% and 30% by weight. As a result of the stereospecificity of the enzymes produced from the strains of the present invention, only the D-enantiomorphs of the hydantoins are hydrolized. As hydantoins however, spontaneously racemize more or less rapidly under the operating conditions, the L-enantiomorphs are completely converted into the corresponding D-α-amino acids.

The quantity of biomass which is added to the reaction mixture depends on the particular affinity of the substrate towards the enzymes. Generally a ratio by weight biomass/hydantoins of between 1/1 and 1/50 can be used.

When the conversion reaction is carried out under optimum conditions a yield of 95–98% is obtained.

The D-α-amino acids prepared with the process of the present invention can be recovered from the reaction medium with the conventional methods such as ion-exchange chromatography or precipitation of the amino acid at its isoelectric point.

The plasmid pSM651 was deposited at the Bureau Voor Schimmelcultures, SK Baarn (Holland) as E.coli SMC305 where it received the deposit number CBS 203.94.

The following experimental examples provide a better illustration of the present invention but do not limit it in any way.

EXAMPLE 1

Extraction of the Chromosomal DNA from A.radiobacter 100 ml of fermentation medium having the following composition: 1% glucose, 0.3% yeast extract, 1.36% $KH_2PO_4$, 0.02% $MgSO_4.7H_2O$ (pH 7.0) were inoculated with the strain A.radiobacter (NRRLB 11291) and maintained under stirring (220 rpm) at 30° C. for 24 hours.

The cells were then recovered by centrifugation of the culture broth in an SS34 rotor model Sorvall RC-5B (at 4° C. and 5000 rpm for 10 minutes) and then washed (2×120 ml) with a solution (TE) containing 1 mM EDTA, 10 mM Tris-HCl, pH 7.4. The resulting suspension was centrifuged again as above and the cells were recovered and resuspended in 9.5 ml of TE solution. After adding 0.5 ml of 10% SDS (sodium dodecylsulphate) and 50 μl of a solution of Proteinase K (20 mg/ml), the suspension was incubated at 37° C. for 1 hour.

1.8 ml of NaCl 5 M and 1.5 ml of a solution consisting of 10% hexadecyltrimethyl ammonium bromide (CTAB) in 0.7 M NaCl were subsequently added and the resulting solution was incubated at 65° C. for 20 minutes. The solution was then deproteinized with an equal volume of chloroform/isoamyl alcohol (24/1, v/v) and the DNA was precipitated with 0.6 volumes of isopropanol. The DNA was washed with 1 ml of ethanol (70%) and recovered with a glass rod. The recovered DNA was finally dissolved in 4 ml of TE and its concentration was determined by spectrophotometry at 260 nm.

The chromosomal DNA was purified again by centrifugation on a gradient of CsCl (1%) containing 0.1 mg/ml of ethidium bromide (55,000 rpm for 16 hours in a Beckman rotor V65Ti).

The DNA band was visualized under a UV light and the ethidium bromide was removed by extraction with butanol saturated in $H_2O$. After dialysis against a TE buffer, the DNA was precipitated with ethanol and resuspended in the desired volume.

EXAMPLE 2

Construction of a Genomic Bank of A.radiobacter

Aliquots (10 μg) of the DNA thus obtained were digested, separately, with 25 units of each of the restriction enzymes EcoRI, PstI, BamHI, SacI, and SphI (Boehringer) operating according to the instructions of the producer.

After blocking the enzymatic reactions at 65° C. for 10 minutes, the reaction mixtures were charged onto agar gel at 0.8% and run at 100 volts for 2 hours. The DNA bands, visualized by coloring with EtBr (0.5 gamma/ml), were then transferred onto a nylon filter (Boehringer) and after lysis with NaOH, the DNA was immobilized according to the Southern blot technique (Maniatis et al., "Molecular Cloning: a practical laboratory manual", Cold Spring Harbor, N.Y., 1982).

The filter was hybridized at 45° C. with each of the degenerated oligonucleotides, conceived on the basis of the amino-end of the carbamylase of Comamonas sp. E222c (Ogawa et al., (1993), Eur. J. Biochem., 212: 685–691), having the sequence:

```
1) 5'CGA ATT GTA AAT TAT GCA GCA GC 3'(SEQ ID NO:1)

A G   C   G   C   C   G   G(SEQ ID NO:2)

C   A   C           C   C(SEQ ID NO:3)

T       T           T   T(SEQ ID NO:4)

2) 5'GGA CCA ATT CAA CGA GC 3'(SEQ ID NO:5)

G   G   C   G   G(SEQ ID NO:6)

C   C   A       C(SEQ ID NO:7)

T   T           T(SEQ ID NO:8)

3) 5'CGA GCA GAT GTA ATG GA 3'(SEQ ID NO:9)

A G   G   C   G(SEQ ID NO:10)

C   C       C(SEQ ID NO:11)

T   T       T(SEQ ID NO:12)
```

These oligonucleotides were synthesized using the automatic System OLIGO 1000 system of Beckmann and then marked at the 5' end using the kit DIG SYSTEM (Boehringer). The hydration reaction with probe 2 gave positive signals. In particular, the DNA digested with BamHI generated a fragment of about 4000 bp capable of hybridizing the probes.

To isolate the BamHI fragment thus identified, 10 μg of chromosomal DNA were suspended in 50 μl of buffer 10 mM Tris-HCl pH 8, 100 mM NaCl, 5 mM MgCl$_2$, 1 mM 2-mercaptoethanol and incubated at 37° C. for 4–5 hours in the presence of 25 U of the enzyme BamHI.

The digestion mixture was then subjected to electrophoresis on agar gel at 0.8% and, after colouring with EtBr, DNA fragments of 3,500–4,500 bp were electroeluated in the electrophoresis buffer (Maniatis et al. "Molecular Cloning: a practical laboratory manual", Cold Spring Habor, N.Y. 1982).

The chromosomal DNA fragments in the plasmid pUC18 (BRL) were then cloned. In practice, 20 ng of this plasmid, previously linearized with the restriction enzyme BamHI, were ligated with 100 ng of the chromosomal DNA fragments in 20 μl of mixture containing 66 mM Tris-HCl pH 7.6, 1 mM ATP, 10 mM MgCl$_2$, 10 mM Dithiotreitol (DTT), in the presence of 1 U of T4 DNA ligase, at 16° C. for a night.

The ligase mixture was used for transforming cells of E.coli JM101 (BRL) made competent with 50 mM CaC$_2$ (Dagert, M. and Ehrlich (1979), Gene, 6:23).

The transformants were subsequently selected on plates of LB medium (8 g/l Bactotryptone (DIFCO), 5 g/l NaCl, 15 g/l Agar (DIFCO), 0.5 g/l yeast extract) to which 40 μg/ml of X-Gal (5-bromo-4-chloro-3-indolyl-D-thio-galactopyranoside) and 100 μg/ml of ampicillin had been added.

Operating as described above numerous positive recombinant colonies (white) were obtained which were easily distinguishable from those not recombinant (blue).

The positive clones were transferred onto nylon filters (Boehringer) and the DNA extracted from these clones was hybridized under the same conditions using probe 2 which had responded positively to hybridation with the chromosomal DNA.

The plasmids extracted from the clones which gave a positive signal were sequenced using the Sequenase version 2.0 Kit (United States Biochemical). One of these plasmids, containing the complete carbamylase gene (915 bp) was called pSM652.

FIG. 4 shows the nucleotidic and amino acidic sequence of carbamylase.

EXAMPLE 3

Isolation of the Hydantoinase Gene of *A.radiobacter*

Analysis of the plasmid pSM652 showed the presence of a second incomplete ORF, situated on the other strand with respect to the carbamylase gene, which showed a homology with urease portions isolated from various microorganisms.

As ureases, like hydantoinases, are enzymes belonging to the group of amidohydrolases, it was assumed that the incomplete ORF corresponded to that of hydantoinase. The assumption was then confirmed by enzymatic activity tests carried out on cellular extracts of cells carrying the identified gene.

In order to isolate the whole nucleotidic sequence encoding the hydantoinase, the same Southern Blot used for isolating the carbamylase was hybridized using as probe the oligonucleotide having the sequence: 5' ATC GTA ACC GCG GAC GGG ATT TCT CCC 3' (SEQ ID NO: 13).

This oligonucleotide, homologous to the 5' end region of the nucleotidic sequence of identified partial ORF, was synthesized and marked as shown in example 2. Among the positive bands for this probe a band of about 3500 bp obtained from the digestion of the DNA with the enzyme SacI, was identified.

Operating as shown in example 2 a genomic bank of chromosomal DNA of *A.radiobacter* digested with SacI was then constructed. Screening of this bank led to the isolation of the plasmid pSM653 containing the whole gene for hydantoinase whose nucleotide and amino acid sequence is shown in FIG. 5.

EXAMPLE 4

Cloning of the Carbamylase Gene

1) Amplification of the Carbamylase Gene

The plasmid pSM652 was amplified by the Polymerase Chain Reaction (PCR) technique, according to the indications specified by Leung et al. (Leung D. W., Chen E., Goeddel D. V., Technique—a journal of methods in cell and molecular biology, 1, No. 1 (1989): pages 11–15), using the pair of oligonucleotides:

```
                                        (SEQ ID NO:14)
(1)  5' GGG AAT TCT TAT GAC ACG TCA G 3' (FORWARD)
           EcoRI (SEQ ID NO:15)
(2)  5' CCC AAG CTT CAA AAT TCC GCG AT 3' (REVERSE)
           HindIII
```

The oligonucleotide (2) also allowed the restriction site EcoRI present inside the carbamylase gene near 3' end, to be eliminated.

The amplification was carried out in a DNA Thermal Cycler 480 apparatus (Perkin—Elmer Cetus) using a reaction mixture (100 μl) containing 10 mM Tris HCl pH 8.3, 1.5 mM MgCl$_2$, 50 mM KCl, 0.01% (weight/volume) of gelatine, 1 ng of pSM652, 1 µM of the two primers, 200 µM of dNTP, 0.5 Units of Taq polymerase (Perkin Elmer).

A drop of mineral oil is added and the mixture is denatured for 4 minutes at 94° C. and the cyclic program is started, which comprises:
1 minute at 94° C. (denaturation)
1 minute at 55° C. (annealing)
2 minutes at 72° C. (elongation)
for a total of 30 cycles, followed by 8 minutes at 72° C. (final extension).

The amplification product thus obtained was treated with phenol-chloroform (1:1), precipitated with NaCl (1/10 vol/vol) and EtOH (2 vol) and resuspended in 20 µl of $H_2O$. After cutting with the restriction enzymes EcoRI and HindIII (5 U) suitable for cloning into the plasmid pSM671 (CBS 205.94) the DNA fragments were purified on low-melting gel (SeaPlaque, FMC BioProducts) at 1.0% and the bands eluated by the gel were treated with GElase (Epicentre Technologies) (1 U every 300 µg of gel weighed) for 1.5 hours at 45° C.

At the same time, 50 ng of the plasmid pSM671 were cut with the same restriction enzymes.

The plasmid and fragments were ligated in 10 µl of reaction mixture (DNA 20 ng/ml) and 2 µl of this mixture were used for transforming cells of E.coli 71/18 made competent with $CaCl_2$ (Dagert and Ehrlich, Gene, 6: 23, 1979). The transformants were selected on plates of LB medium containing 20 µg/ml of chloramphenicol.

The plasmid DNA extracted from the positive clones was analyzed to verify exact insertion into the carbamylase gene and the absence of possible errors caused by the amplification.

One of these plasmids was called pSM637.

The strain of E.coli containing the plasmid pSM637 was called SMC307.

Cells of B.subtilis SMS108 NRRLB-15.898 made competent as described in "Molecular Biology Methods for Bacillus", (1990) (Harwood and Cutting (eds) Wiley and Sons) were transformed with 100 ng of the plasmid pSM637 operating according to the known techniques, and the transformed strain was called SMS374.

EXAMPLE 5
Expression of the Carbamylase Gene in E.coli and B.subtilis

The object of the experiment was to verify the ability of the transformed strains (E.coli SMC307 and B.subtilis SMS 374) to express the carbamylase gene without inducers.

A preculture on slant of the strain E.coli SMS307 and B.subtilis SMS 374 was inoculated into two 100 ml flasks containing, respectively, 10 ml of LB medium to which 20 µg/ml of chloramphenicol had been added and 10 ml of VY medium to which 5 µg/ml of chloramphenicol had been added. The flasks were incubated, under stirring, (220 rpm), at 37° C. for 16 hours.

The cells were recovered by centrifugation (12,000 rpm, 4° C., for 1 minute) of the two culture broths, resuspended in 300 µl of buffer 20 mM Tris-HCl pH 7.5, 20 mM BMeOH, 20% glycerol and lysed by sonication (Soniprep150, MSE 1 minute impulses, at average voltage). Aliquots (15 µl) of the two lysates were charged onto polyacryalamide gel at 10% and run at 20 mA for three hours. The proteic bands were visualized by colouring with Coomassie R-250 (Laemmli, Nature: 227, 680, 1970). After colouring with Coomassie a proteic band was revealed with a molecular weight of 34,000 D absent in the extracts of untransformed strains B.subtilis SMS108 and E.coli 71/18. In addition, densitometric analysis carried out on the same gel coloured with Coomassie showed that this protein was expressed in both of the transformed strains as one of the prevalent proteins (10% with respect to the total proteins).

EXAMPLE 6
Cloning of the Hydantoinase Gene

The plasmid pSM653 (1 µg) was digested with the restriction enzymes EcoRV and SalI (4 U) (Boehringer) at 37° C. for 1 hour.

The digestion mixture was then subjected to electrophoresis on agar gel at 0.8% (low melting) and, after colouring with EtBr, the DNA band corresponding to an EcoRV-SalI fragment of 1300 bp was recut and the DNA extracted with the Gelase TM method (EPICENTRE Technologies). As this fragment has a small region missing at the 5' end and a portion of 70 bp at 3' end, the whole hydantoinase gene was reconstructed using two linkers having the sequence:

```
                                           (SEQ ID NO:16)
LINKER 5'
5'AATTCTTATG GAT 3'
  EcoRI
```

```
                                           (SEQ ID NO:17)
LINKER 3'
5'TCGACGAGGG AACCTACGTG GGGGCGCCGA CGGATGGCCA
  SalI
  GTTCCGGAAG CGCCGCAAAT ACAAGCAATA AGGAGG 3'
                                       EcoRI
```

40 ng of the 1300 bp fragment, 40 ng of the linker 3', 10 ng of the linker 5' and 50 ng of the plasmid pSM671 CBS 205.94, previously linearized with EcoRI, were then ligated in a ligase mixture containing 1 U of T4 DNA ligase, incubating at 12° C. for 16 hours. The ligase mixture was subsequently used to transform competent cells of E.coli 71/18 and the transformants were selected on plates of LB medium to which 20 µg/ml of chloramphenicol had been added.

The plasmid DNAs isolated from some of the positive clones were analyzed to identify the clones containing the complete sequence of the hydantoinase gene.

One of these plasmids was called pSM650 and the strain of E.coli containing said plasmid was marked with the abbreviation SMC308. 100 ng of the plasmid pSM650 were used to transform competent cells of B.subtilis SMS108. The resulting strain was called SMS375.

EXAMPLE 7
Expression of the Hydantoinase Gene in E.coli and B.subtilis

The object of the experiment was to verify the capacity of the transformed strains (E.coli SMS308 and B.subtilis SMS375) to express the hydantoinase gene without inducers.

A preculture on slant of the strain E.coli SMS308 and B.subtilis SMS375 was inoculated into two 50 ml flasks containing, respectively, 10 ml of LB medium to which 5 µg/ml of chloramphenicol had been added and 10 ml of VY medium to which 20 µg/ml of chloramphenicol had been added. The flasks were incubated, under gentle stirring, (220 rpm), at 37° C. for 16 hours.

The cells were recovered by centrifugation (12,000 rpm, 4° C., for 1 minute) of the two culture broths, resuspended in 300 µl of buffer 20 mM Tris-HCl pH 7.5, 20 mM BMeOH, 20% glycerol and lysed by sonication (1 minute impulses, at average voltage). Aliquots (15 µl) of the two lysates were charged onto polyacryalamide gel at 10% and run at 20 mA for three hours. The proteic bands were visualized by colouring with Coomassie R-250 (Laemmli, Nature: 227, 680, 1970). After colouring with Coomassie a proteic band was revealed with a molecular weight of 50,000 Daltons absent in the extracts of untransformed strains *B.subtilis* SMS108 and *E.coli* 71/18. In addition, densitometric analysis carried out on the same gel coloured with Coomassie showed that this protein was expressed in the two transformed strains as one of the prevalent proteins (10% with respect to the total proteins).

EXAMPLE 8
Cloning of the Hydantoinase-carbamylase Operon

The plasmid pSM650 (1 µg) was digested with the enzyme EcoRI (5 U) at 37° C. for 1 hour. The EcoRI-EcoRI fragment of about 1380 bp containing the hydantoinase gene was purified by agar gel at 0.8% with the Gelase TM method. 20 ng of this fragment were ligated with 50 ng of the plasmid pSM637 linearized with EcoRI. The reaction was carried out in a ligase buffer containing 1 U of T4 DNA ligase, at 16° C. for 16 hours.

The ligase mixture was used to transform competent cells of *E.coli* 71/18.

The transformants were subsequently selected on plastes of LB medium (8 g/l Bactotryptone (DIFCO), 5 g/l NaCl, 15 g/l Agar (DIFCO), 0.5 g/l yeast extract) to which 20 µg/ml of Chloramphenicol had been added.

The positive clones were analyzed by restriction analysis to verify the correct insertion into the two genes. The plasmid containing the hydantoinase-carbamylase operon was called pSM651 and the strain of *E.coli* containing said plasmid was marked with the abbreviation SMC305.

Competent cells of *B.subtilis* SMS108 were transformed with 100 ng of this plasmid. One of the positive clones was called SMS373.

EXAMPLE 9
Expression of the Hydantoinase-carbamylase Operon

Figures 6A, 6B:
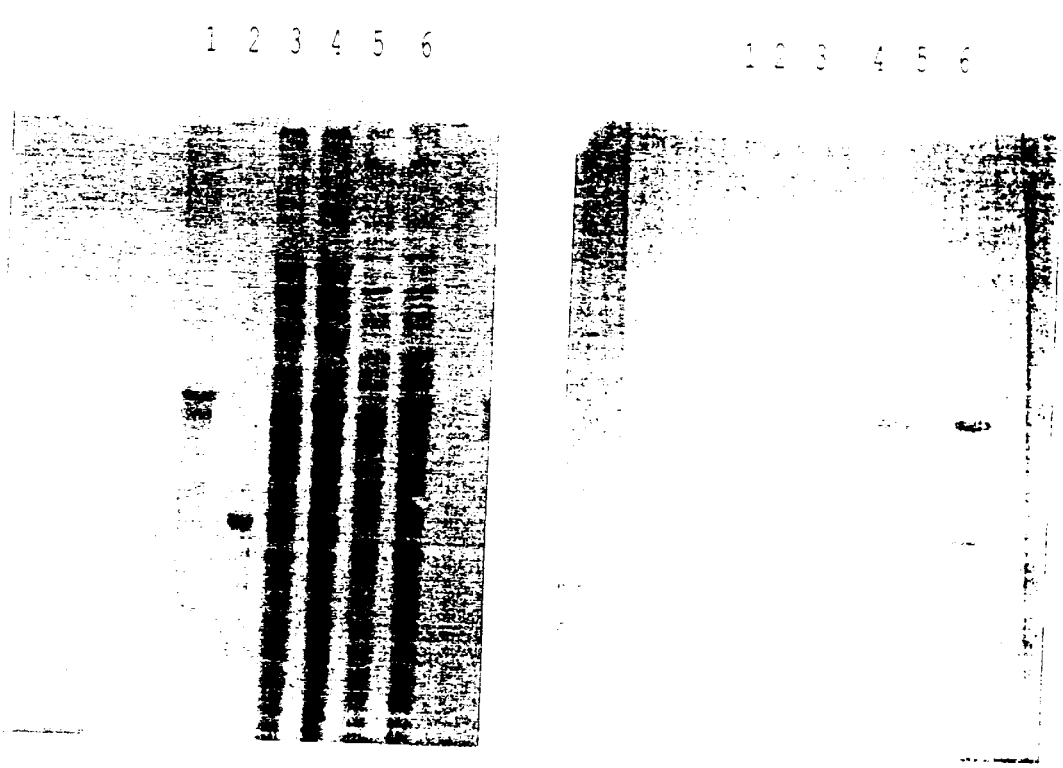
FIGS. 6A–B: SDS-PAGE (A) and Western-Blot (B) of the total proteins extracted from cultures of *E.coli* and *B.subtilis* transformed with the plasmid pSM651 wherein:
line 1: standard hydantoinase
line 2: standard carbamylase
line 3: *E.coli* (pSM671) control
line 4: *E.coli* SMC305
line 5: *B.subtilis* (pSM671) control
line 6: *B.subtilis* SMS373

*E.coli* SMC305 and *B.subtilis* SMS373 were cultured, respectively, in 100 ml of LB medium to which 20 µg of chloramphenicol had been added and in 100 ml of VY medium to which 5 µg of chloramphenicol had been added, at 37° C. for 16 hours, under stirring (200 rpm). The proteic extracts obtained from the cellular lysates were analyzed as described in example 7. The results showed the presence of two proteins corresponding to hydantoinase and carbamylase (FIG. 6 (SEQ ID NO: 19,21)). To evaluate the activity of these enzymes, a reaction kinetics was carried out using 20 mM (D,L) parahydroxyphenyl-hydantoin as substrate or alternatively 5-phenyl-hydantoin (in 200 mM of phosphate buffer pH 8) and following the conversion into the corresponding D-α-amino acid with the evolution of ammonia. The process adopted is described by Weatherburn, M. W., (1967), (Anal. Chem., 39:971).

EXAMPLE 10
Conversion of D,L-5-phenylhydantoin to D-phenylglycine

A suspension of 2 g of D,L-5-phenyl-hydantoin in 100 ml of Na-phosphate 0.2 M buffer pH 8.0 was charged into an apparatus equipped with a stirrer and thermostat-regulated at 40° C. After degassing with nitrogen at 40° C. for 5 minutes, 5 g (humid weight) of biomass was introduced, coming from a culture of *E.coli* SMS305, carried out as described in example 9.

After the apparatus had been hermetically closed, the reaction mixture was maintained under a nitrogen atmosphere, at 40° C. for 24 hours. Polarimetric and thin layer chromatographic analysis (J. of Chromatography, 80: 199–204), 1973) of an aliquot of the reaction mixture showed the complete hydrolysis of the starting substrate to D-phenylglycine.

After separation of the biomass by centrifugation of the reaction mixture at 6000 rpm for 10 minutes, the surnatant was acidified to pH 1.0 with HCl 6 M and charged onto a column (2.6×20 cm) of Amberlite IR 120 (activated with HCl). The column was then washed with water and eluted with an ammonia solution at 5% in water. The eluate was decoloured with decolouring carbon (C.Erba), and the decoloured solution was concentrated under vacuum and brought to pH 5.8. The crystals thus obtained were recovered by filtration and recrystallized from water. The white powder obtained (1.63 g) showed a specific rotation $[\alpha]_D 20=-156°$ (c=1, 1 N HCl). The IR spectrum was in agreement with that of the standard D-phenylglycine.

EXAMPLE 11
Conversion of D,L-5-phenylhydandoin to D-phenylglycine

The same procedure was carried out as in example 10, using 5 g (humid weight) of biomass coming from the culture of *E.coli* SMS305 and 10 g of D,L-5-phenylhydantoin in 100 ml of Na-phosphate 0.2 M buffer pH 8.0. The reaction was carried out under a nitrogen atmosphere, at 40° C. for 90 hours. The white powder obtained (8.1 g) showed a specific rotation $[\alpha]_D 20=31$ 156.5° (c=1, 1 N HCl). The IR spectrum agreed with that of the standard D-phenylglycine.

EXAMPLE 12
Conversion of D,L-5-para-hydroxy-phenylhydantoin to D-para-hydroxy-phenylglycine The same procedure was carried out as in example 10, using 2.5 g (humid weight) of biomass and 1 g of D,L-5-para-hydroxy-phenylhydantoin. The D-para-hydroxy-phenylglycine obtained as a white powder (0.82 g) showed a specific rotation $[a]_D 20=-158°$ (c=1,1 N HCl). The IR spectrum was in agreement with that of the standard D-phenylglycine.

EXAMPLE 13
Conversion of D,L-5-para-hydroxy-phenylhydantoin to D-para-hydroxy-phenylglycine The same procedure was carried out as in example 10, using 2.5 g of biomass (humid weight) obtained from the culture of *E.coli* SMS305 and 8 g of D,L-5-para-hydroxy-phenylhydantoin.

The reaction was carried out under a nitrogen atmosphere, at 40° C. for 170 hours. The D-parahydroxy-phenylglycine obtained as a white powder (6.6 g) showed a specific rotation $[\alpha]_D 20=-157.8°$ (c=1,1 N HCl). The IR spectrum was in agreement with that of the standard D-phenylglycine.

EXAMPLE 14
Conversion of D,L-5-isopropylhydantoin to D-valine

The same procedure was carried out as in example 10, using 5.0 g of biomass (humid weight) obtained from the culture of *E.coli* SMS305 and 2 g of D,L-5-iso-propylhydantoin.

The reaction was carried out under a nitrogen atmosphere, at 40° C. for 240 hours. The D-valine obtained tained as a white powder (0.8 g) showed a specific rotation $[\alpha]_D 20=-27.5°$ (c=5, 6 N HCl). The IR spectrum agreed with that of the standard D-valine.

What is claimed is:

1. A process for the production of D-α-amino acids by the stereospecific conversion of racemic mixtures of 5-substituted hydantoins wherein the conversion reaction is carried out in the presence of a microorganism transformed with the plasmid pSM651 CBS 203.94 capable of expressing at high levels and without inducers an enzymatic system capable of converting said hydantoins into the corresponding D-α-amino acids.

2. A process for the production of D-α-amino acids by the stereospecific conversion of racemic mixtures of 5-substituted hydantoins, wherein the conversion reaction is carried out in the presence of an enzymatic system isolated from a microorganism transformed with the plasmid pSM651 CBS 203.94.

3. The process according to claim 2, wherein said enzymatic system is immobilized on an insoluble support.

4. The process according to claim 1, wherein the microorganisms are selected from the group of *Bacillus subtilis* and *Escherichia coli*.

5. The process according to claim 1, wherein the 5-substituted hydantoin is selected from D,L-5-phenylhydantoin, D,L-5-para-hydroxyphenyl-hydantoin, D,L-5-methylhydantoin, D,L-5-isopropyl-hyantion, D,L-5-thienylhydantoin, D,L-5-para-methoxyphenylhydantoin, D,L-5-para-chloro phenylhydantoin, D,L-5-benzylhydantoin.

6. The process according to claim 5, wherein the hydantoin is D,L-5-para-hydroxyphenyl-hydantoin.

7. The process according to claim 5, wherein the hydantoin is D,L-5-phenylhydantoin.

8. The process according to claim 1, wherein the conversion reaction is carried out at a temperature of between 20° C. and 60° C.

9. The process according to claim 8, wherein the temperature is between 30° and 45° C.

10. The process according to claim 1, wherein the conversion reaction is carried out at a pH of between 6.0 and 10.

11. The process according to claim 10, wherein the pH is between 7.0 and 8.5.

12. The process according to claim 1, wherein the conversion reaction is carried out using a weight ratio biomass/hydantoins of between 1/1 and 1/50.

13. Plasmid pSM651 deposited at the Bureau Voor Schimmelcultures, SK Baarn (Holland) where it has received the deposit number CBS 203.94.

14. A microorganism selected from *Bacillus subtilis* and *Escherichia coli* transformed with the plasmid pSM651.

15. The microorganism according to claim 10, which is *Escherichia coli* SMC305 CBS 203.94.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

CGAATTGTAA ATTATGCAGC AGC                                                23

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AGGATCGTGA ACTACGCGGC GGC                                                23

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGCATAGTCA ATTATGCCGC CGC                                                23

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGTATTGTTA ATTATGCTGC TGC                                                23

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGACCAATTC AACGAGC                      17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGCCGATCC AGCGGGC                      17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGCCCCATAC AACGCGC                      17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGTCCTATTC AACGTGC                      17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CGAGCAGATG TAATGGA                      17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGGGCGGACG TGATGGA                      17

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CGCGCCGATG TCATGGA                                              17

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

CGTGCTGATG TTATGGA                                              17

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ATCGTAACCG CGGACGGGAT TTCTCCC                                   27

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGGAATTCTT ATGACACGTC AG                                        22

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCCAAGCTTC AAAATTCCGC GAT                                       23

(2) INFORMATION FOR SEQ ID NO:16:

(i) SEQUENCE CHARACTERISTICS:
        (A) LENGTH: 13 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AATTCTTATG GAT                                                          13

(2) INFORMATION FOR SEQ ID NO:17:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCGACGAGGG AACCTACGTG GGGGCGCCGA CGGATGGCCA GTTCCGGAAG CGCCGCAAAT        60

ACAAGCAATA AGGAGG                                                       76

(2) INFORMATION FOR SEQ ID NO:18:

(i) SEQUENCE CHARACTERISTICS:
        (A) LENGTH: 915 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Agrobacterium radiobacter (ix) FEATURE:
        (A) NAME/KEY: CDS
        (B) LOCATION: 1..915

(xi) SEQUENCE DESCRIPTION: SEQ ID NO:18:

```
ATG ACA CGT CAG ATG ATA CTT GCT GTC GGA CAG CAA GGC CCC ATC GCG         48
Met Thr Arg Gln Met Ile Leu Ala Val Gly Gln Gln Gly Pro Ile Ala
 1               5                  10                  15

CGA GCG GAG ACA CGC GAA CAG GTG GTT GGC CGC CTC CTC GAC ATG TTG         96
Arg Ala Glu Thr Arg Glu Gln Val Val Gly Arg Leu Leu Asp Met Leu
             20                  25                  30

ACG AAC GCA GCC AGC CGG GGC GTG AAC TTC ATC GTC TTT CCC GAG CTT         144
Thr Asn Ala Ala Ser Arg Gly Val Asn Phe Ile Val Phe Pro Glu Leu
         35                  40                  45

GCG CTC ACG ACC TTC TTC CCG CGC TGG CAT TTC ACC GAC GAG GCC GAG         192
Ala Leu Thr Thr Phe Phe Pro Arg Trp His Phe Thr Asp Glu Ala Glu
     50                  55                  60

CTC GAT AGC TTC TAT GAG ACC GAA ATG CCC GGC CCG GTG GTC CGT CCA         240
Leu Asp Ser Phe Tyr Glu Thr Glu Met Pro Gly Pro Val Val Arg Pro
 65                  70                  75                  80

CTC TTT GAG ACG GCC GCC GAA CTC GGG ATC GGC TTC AAT CTG GGC TAC         288
Leu Phe Glu Thr Ala Ala Glu Leu Gly Ile Gly Phe Asn Leu Gly Tyr
                 85                  90                  95

GCC GAA CTC GTC GTC GAA GGC GGC GTC AAG CGT CGC TTC AAC ACG TCC         336
Ala Glu Leu Val Val Glu Gly Gly Val Lys Arg Arg Phe Asn Thr Ser
            100                 105                 110

ATT CTG GTG GAT AAG TCA GGC AAG ATC GTC GGC AAG TAT CGT AAG ATC         384
Ile Leu Val Asp Lys Ser Gly Lys Ile Val Gly Lys Tyr Arg Lys Ile
        115                 120                 125
```

```
CAT TTG CCG GGT CAC AAG GAG TAC GAG GCC TAC CGG CCG TTC CAG CAT    432
His Leu Pro Gly His Lys Glu Tyr Glu Ala Tyr Arg Pro Phe Gln His
    130                 135                 140

CTT GAA AAG CGT TAT TTC GAG CCG GGC GAT CTC GGC TTC CCG GTC TAT    480
Leu Glu Lys Arg Tyr Phe Glu Pro Gly Asp Leu Gly Phe Pro Val Tyr
145                 150                 155                 160

GAC GTC GAC GCC GCG AAA ATG GGG ATG TTC ATC TGC AAC GAT CGC CGC    528
Asp Val Asp Ala Ala Lys Met Gly Met Phe Ile Cys Asn Asp Arg Arg
                165                 170                 175

TGG CCT GAA ACG TGG CGG GTG ATG GGA CTT AAG GGC GCC GAG ATC ATC    576
Trp Pro Glu Thr Trp Arg Val Met Gly Leu Lys Gly Ala Glu Ile Ile
            180                 185                 190

TGC GGC GGC TAC AAC ACG CCG ACC CAC AAT CCC CCC GTT CCC CAG CAC    624
Cys Gly Gly Tyr Asn Thr Pro Thr His Asn Pro Pro Val Pro Gln His
        195                 200                 205

GAC CAT CTG ACG TCC TTC CAC CAC CTT CTG TCG ATG CAG GCC GGG TCG    672
Asp His Leu Thr Ser Phe His His Leu Leu Ser Met Gln Ala Gly Ser
    210                 215                 220

TAC CAA AAC GGC GCC TGG TCC GCG GCG GCC GGC AAG GTC GGC ATG GAG    720
Tyr Gln Asn Gly Ala Trp Ser Ala Ala Ala Gly Lys Val Gly Met Glu
225                 230                 235                 240

GAG GGG TGC ATG CTG CTC GGC CAT TCG TGC ATC GTG GCG CCG ACC GGC    768
Glu Gly Cys Met Leu Leu Gly His Ser Cys Ile Val Ala Pro Thr Gly
                245                 250                 255

GAA ATC GTT GCC CTG ACC ACG ACG TTG GAA GAC GAG GTG ATC ACC GCC    816
Glu Ile Val Ala Leu Thr Thr Thr Leu Glu Asp Glu Val Ile Thr Ala
            260                 265                 270

GCC GTC GAT CTC GAC CGC TGC CGG GAA CTG CGC GAA CAC ATC TTC AAT    864
Ala Val Asp Leu Asp Arg Cys Arg Glu Leu Arg Glu His Ile Phe Asn
        275                 280                 285

TTC AAA GCC CAT CGT CAG CCA CAG CAC TAC GGT CTG ATC GCG GAA TTT    912
Phe Lys Ala His Arg Gln Pro Gln His Tyr Gly Leu Ile Ala Glu Phe
    290                 295                 300

TGA                                                                915
 *
305

(2) INFORMATION FOR SEQ ID NO:19:

(i) SEQUENCE CHARACTERISTICS:
        (A) LENGTH: 304 amino acids
        (B) TYPE: amino acid
        (D) TOPOLOGY: linear (ii) MOLECULE TYPE: protein (xi) SEQUENCE DESCRIPTION: SEQ ID NO:19:

Met Thr Arg Gln Met Ile Leu Ala Val Gly Gln Gln Gly Pro Ile Ala
 1               5                  10                  15

Arg Ala Glu Thr Arg Glu Gln Val Val Gly Arg Leu Leu Asp Met Leu
            20                  25                  30

Thr Asn Ala Ala Ser Arg Gly Val Asn Phe Ile Val Phe Pro Glu Leu
        35                  40                  45

Ala Leu Thr Thr Phe Phe Pro Arg Trp His Phe Thr Asp Glu Ala Glu
    50                  55                  60

Leu Asp Ser Phe Tyr Glu Thr Glu Met Pro Gly Pro Val Val Arg Pro
65                  70                  75                  80

Leu Phe Glu Thr Ala Ala Glu Leu Gly Ile Gly Phe Asn Leu Gly Tyr
                85                  90                  95

Ala Glu Leu Val Val Glu Gly Gly Val Lys Arg Arg Phe Asn Thr Ser
```

```
            100                 105                 110
Ile Leu Val Asp Lys Ser Gly Lys Ile Val Gly Lys Tyr Arg Lys Ile
        115                 120                 125

His Leu Pro Gly His Lys Glu Tyr Glu Ala Tyr Arg Pro Phe Gln His
    130                 135                 140

Leu Glu Lys Arg Tyr Phe Glu Pro Gly Asp Leu Gly Phe Pro Val Tyr
145                 150                 155                 160

Asp Val Asp Ala Ala Lys Met Gly Met Phe Ile Cys Asn Asp Arg Arg
                165                 170                 175

Trp Pro Glu Thr Trp Arg Val Met Gly Leu Lys Gly Ala Glu Ile Ile
            180                 185                 190

Cys Gly Gly Tyr Asn Thr Pro Thr His Asn Pro Pro Val Pro Gln His
        195                 200                 205

Asp His Leu Thr Ser Phe His His Leu Leu Ser Met Gln Ala Gly Ser
    210                 215                 220

Tyr Gln Asn Gly Ala Trp Ser Ala Ala Ala Gly Lys Val Gly Met Glu
225                 230                 235                 240

Glu Gly Cys Met Leu Leu Gly His Ser Cys Ile Val Ala Pro Thr Gly
                245                 250                 255

Glu Ile Val Ala Leu Thr Thr Thr Leu Glu Asp Glu Val Ile Thr Ala
            260                 265                 270

Ala Val Asp Leu Asp Arg Cys Arg Glu Leu Arg Glu His Ile Phe Asn
        275                 280                 285

Phe Lys Ala His Arg Gln Pro Gln His Tyr Gly Leu Ile Ala Glu Phe
    290                 295                 300

*
305

(2) INFORMATION FOR SEQ ID NO:20:

(i) SEQUENCE CHARACTERISTICS:
        (A) LENGTH: 1374 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Agrobacterium radiobacter (ix) FEATURE:
        (A) NAME/KEY: CDS
        (B) LOCATION: 1..1374

(xi) SEQUENCE DESCRIPTION: SEQ ID NO:20:

ATG GAT ATC ATC ATC AAG AAC GGA ACC ATC GTA ACC GCG GAC GGG ATT      48
Met Asp Ile Ile Ile Lys Asn Gly Thr Ile Val Thr Ala Asp Gly Ile
                310                 315                 320

TCT CCC GCC GAT CTC GGA ATC AAG GAT GGC AAG ATC GCC CAG ATC GGC      96
Ser Pro Ala Asp Leu Gly Ile Lys Asp Gly Lys Ile Ala Gln Ile Gly
            325                 330                 335

GGA ACG TTC GGC CCG GCC GGC CGG ACA ATC GAC GCC TCC GGC CGC TAC     144
Gly Thr Phe Gly Pro Ala Gly Arg Thr Ile Asp Ala Ser Gly Arg Tyr
        340                 345                 350

GTT TTT CCG GGC GGC ATC GAC GTT CAT ACG CAT GTC GAG ACG GTC AGC     192
Val Phe Pro Gly Gly Ile Asp Val His Thr His Val Glu Thr Val Ser
    355                 360                 365

TTC AAC ACG CAG TCG GCC GAC ACA TTC GCA ACC GCG ACG GTC GCG GCC     240
Phe Asn Thr Gln Ser Ala Asp Thr Phe Ala Thr Ala Thr Val Ala Ala
```

-continued

```
              370               375               380               385
GCC TGT GGC GGC ACG ACG ACC ATC GTC GAT TTC TGC CAG CAG GAC CGC      288
Ala Cys Gly Gly Thr Thr Thr Ile Val Asp Phe Cys Gln Gln Asp Arg
                    390               395               400

GGC CAT AGC CTG AGG GAG GCG GTC GCC AAA TGG GAC GGC ATG GCC GGC      336
Gly His Ser Leu Arg Glu Ala Val Ala Lys Trp Asp Gly Met Ala Gly
            405               410               415

GGC AAG TCG GCG ATC GAC TAC GGC TAC CAT ATC ATC GTG CTC GAT CCG      384
Gly Lys Ser Ala Ile Asp Tyr Gly Tyr His Ile Ile Val Leu Asp Pro
            420               425               430

ACT GAT AGC GTG ATC GAG GAG CTA GAG GTA CTG CCA GAT CTC GGC ATC      432
Thr Asp Ser Val Ile Glu Glu Leu Glu Val Leu Pro Asp Leu Gly Ile
            435               440               445

ACC TCC TTC AAG GTC TTC ATG GCT TAT CGC GGC ATG AAC ATG ATC GAC      480
Thr Ser Phe Lys Val Phe Met Ala Tyr Arg Gly Met Asn Met Ile Asp
450               455               460               465

GAC GTG ACA CTG CTC AGG ACG CTC GAC AAG GCC GCC AAG ACT GGG TCA      528
Asp Val Thr Leu Leu Arg Thr Leu Asp Lys Ala Ala Lys Thr Gly Ser
            470               475               480

CTC GTC ATG GTG CAC GCG GAG AAC GGC GAC GCC GCC GAC TAT CTT CGC      576
Leu Val Met Val His Ala Glu Asn Gly Asp Ala Ala Asp Tyr Leu Arg
            485               490               495

GAC AAG TTC GTC GCC GAT GGC AAA ACG GCG CCG ATC TAC CAC GCG CTC      624
Asp Lys Phe Val Ala Asp Gly Lys Thr Ala Pro Ile Tyr His Ala Leu
            500               505               510

AGC CGT CCG CCC CGG GTC GAA GCC GAG GCG ACC GCG AGG GCC CTC GCC      672
Ser Arg Pro Pro Arg Val Glu Ala Glu Ala Thr Ala Arg Ala Leu Ala
            515               520               525

CTG GCG GAA ATC GTC AAC GCC CCG ATC TAC ATC GTG CAT CTG ACC TGC      720
Leu Ala Glu Ile Val Asn Ala Pro Ile Tyr Ile Val His Leu Thr Cys
530               535               540               545

GAA GAA TCC TTC GAC GAG TTG ATG CGG GCA AAG GCT CGG GGT GTC CAC      768
Glu Glu Ser Phe Asp Glu Leu Met Arg Ala Lys Ala Arg Gly Val His
                    550               555               560

GCC CTG GCC GAA ACC TGC ACA CAA TAC CTC TAC CTC ACC AAG GAC GAC      816
Ala Leu Ala Glu Thr Cys Thr Gln Tyr Leu Tyr Leu Thr Lys Asp Asp
                565               570               575

CTG GAG CGG CCG GAT TTC GAG GGC GCG AAG TAT GTT TTC ACC CCG CCT      864
Leu Glu Arg Pro Asp Phe Glu Gly Ala Lys Tyr Val Phe Thr Pro Pro
            580               585               590

CCG CGC ACG AAG AAG GAC CAG GAA ATC CTC TGG AAC GCA CTC CGG AAC      912
Pro Arg Thr Lys Lys Asp Gln Glu Ile Leu Trp Asn Ala Leu Arg Asn
            595               600               605

GGG GTC CTC GAA ACG GTC TCC TCG GAC CAT TGT TCC TGG CTC TTC GAG      960
Gly Val Leu Glu Thr Val Ser Ser Asp His Cys Ser Trp Leu Phe Glu
610               615               620               625

GGG CAC AAG GAT CGG GGC AGG AAC GAC TTC CGC GCC ATC CCG AAC GGA     1008
Gly His Lys Asp Arg Gly Arg Asn Asp Phe Arg Ala Ile Pro Asn Gly
            630               635               640

GCG CCG GGC GTC GAG GAG CGG CTG ATG ATG GTC TAT CAG GGC GTC AAC     1056
Ala Pro Gly Val Glu Glu Arg Leu Met Met Val Tyr Gln Gly Val Asn
            645               650               655

GAA GGC CGC ATT TCC CTC ACC CAG TTC GTA GAA CTG GTC GCC ACG CGC     1104
Glu Gly Arg Ile Ser Leu Thr Gln Phe Val Glu Leu Val Ala Thr Arg
            660               665               670

CCG GCC AAG GTC TTC GGC ATG TTC CCG GAA AAA GGA ACG GTC GCG GTC     1152
Pro Ala Lys Val Phe Gly Met Phe Pro Glu Lys Gly Thr Val Ala Val
            675               680               685

GGT TCG GAT GCC GAC ATC GTC CTT TGG GAT CCC GAG GCT GAA ATG GTG     1200
```

-continued

```
Gly Ser Asp Ala Asp Ile Val Leu Trp Asp Pro Glu Ala Glu Met Val
690                 695                 700                 705

ATC GAA CAA AGC GCC ATG CAT AAC GCC ATG GAT TAC TCC TCC TAC GAG    1248
Ile Glu Gln Ser Ala Met His Asn Ala Met Asp Tyr Ser Ser Tyr Glu
                710                 715                 720

GGA CAC AAG ATC AAG GGC GTG CCG AAG ACA GTG CTG CTG CGT GGC AAG    1296
Gly His Lys Ile Lys Gly Val Pro Lys Thr Val Leu Leu Arg Gly Lys
                725                 730                 735

GTG ATC GTC GAC GAG GGA ACC TAC GTG GGG GCG CCG ACG GAT GGC CAG    1344
Val Ile Val Asp Glu Gly Thr Tyr Val Gly Ala Pro Thr Asp Gly Gln
                740                 745                 750

TTC CGG AAG CGC CGC AAA TAC AAG CAA TAA                            1374
Phe Arg Lys Arg Arg Lys Tyr Lys Gln *
    755                 760
```

(2) INFORMATION FOR SEQ ID NO:21:

(i) SEQUENCE CHARACTERISTICS:
        (A) LENGTH:  457 amino acids
        (B) TYPE: amino acid
        (D) TOPOLOGY: linear (ii) MOLECULE TYPE: protein (xi) SEQUENCE DESCRIPTION: SEQ ID NO:21:

```
Met Asp Ile Ile Ile Lys Asn Gly Thr Ile Val Thr Ala Asp Gly Ile
1               5                   10                  15

Ser Pro Ala Asp Leu Gly Ile Lys Asp Gly Lys Ile Ala Gln Ile Gly
                20                  25                  30

Gly Thr Phe Gly Pro Ala Gly Arg Thr Ile Asp Ala Ser Gly Arg Tyr
            35                  40                  45

Val Phe Pro Gly Gly Ile Asp Val His Thr His Val Glu Thr Val Ser
        50                  55                  60

Phe Asn Thr Gln Ser Ala Asp Thr Phe Ala Thr Ala Thr Val Ala Ala
65                  70                  75                  80

Ala Cys Gly Gly Thr Thr Thr Ile Val Asp Phe Cys Gln Gln Asp Arg
                85                  90                  95

Gly His Ser Leu Arg Glu Ala Val Ala Lys Trp Asp Gly Met Ala Gly
                100                 105                 110

Gly Lys Ser Ala Ile Asp Tyr Gly Tyr His Ile Ile Val Leu Asp Pro
            115                 120                 125

Thr Asp Ser Val Ile Glu Glu Leu Glu Val Leu Pro Asp Leu Gly Ile
        130                 135                 140

Thr Ser Phe Lys Val Phe Met Ala Tyr Arg Gly Met Asn Met Ile Asp
145                 150                 155                 160

Asp Val Thr Leu Leu Arg Thr Leu Asp Lys Ala Ala Lys Thr Gly Ser
                165                 170                 175

Leu Val Met Val His Ala Glu Asn Gly Asp Ala Ala Asp Tyr Leu Arg
                180                 185                 190

Asp Lys Phe Val Ala Asp Gly Lys Thr Ala Pro Ile Tyr His Ala Leu
            195                 200                 205

Ser Arg Pro Pro Arg Val Glu Ala Glu Ala Thr Ala Arg Ala Leu Ala
        210                 215                 220

Leu Ala Glu Ile Val Asn Ala Pro Ile Tyr Ile Val His Leu Thr Cys
225                 230                 235                 240

Glu Glu Ser Phe Asp Glu Leu Met Arg Ala Lys Ala Arg Gly Val His
                245                 250                 255
```

```
Ala Leu Ala Glu Thr Cys Thr Gln Tyr Leu Tyr Leu Thr Lys Asp Asp
            260                 265                 270

Leu Glu Arg Pro Asp Phe Glu Gly Ala Lys Tyr Val Phe Thr Pro Pro
        275                 280                 285

Pro Arg Thr Lys Lys Asp Gln Glu Ile Leu Trp Asn Ala Leu Arg Asn
    290                 295                 300

Gly Val Leu Glu Thr Val Ser Ser Asp His Cys Ser Trp Leu Phe Glu
305                 310                 315                 320

Gly His Lys Asp Arg Gly Arg Asn Asp Phe Arg Ala Ile Pro Asn Gly
                325                 330                 335

Ala Pro Gly Val Glu Glu Arg Leu Met Met Val Tyr Gln Gly Val Asn
            340                 345                 350

Glu Gly Arg Ile Ser Leu Thr Gln Phe Val Glu Leu Val Ala Thr Arg
            355                 360                 365

Pro Ala Lys Val Phe Gly Met Phe Pro Glu Lys Gly Thr Val Ala Val
    370                 375                 380

Gly Ser Asp Ala Asp Ile Val Leu Trp Asp Pro Glu Ala Glu Met Val
385                 390                 395                 400

Ile Glu Gln Ser Ala Met His Asn Ala Met Asp Tyr Ser Ser Tyr Glu
            405                 410                 415

Gly His Lys Ile Lys Gly Val Pro Lys Thr Val Leu Leu Arg Gly Lys
            420                 425                 430

Val Ile Val Asp Glu Gly Thr Tyr Val Gly Ala Pro Thr Asp Gly Gln
            435                 440                 445

Phe Arg Lys Arg Arg Lys Tyr Lys Gln
    450                 455
```